US010925914B2

(12) United States Patent
Choi et al.

(10) Patent No.: US 10,925,914 B2
(45) Date of Patent: Feb. 23, 2021

(54) METHOD FOR ALLEVIATING DEPRESSION USING A HEALTH FUNCTIONAL FOOD CONTAINING *VACCINIUM BRACTEATUM* THUNB FRUIT EXTRACT (71) Applicant: JEONNAM BIOINDUSTRY FOUNDATION, Jeollanam-do (KR)

(72) Inventors: Chul Yung Choi, Gwangju (KR); Jae Yong Kim, Jeollanam-do (KR); Gyu Ok Lee, Jeollanam-do (KR); Ja Won Shin, Jeollanam-do (KR); Hu Won Kang, Gwangju (KR); Ara Jo, Gwangju (KR); Hak Joon Choi, Gwangju (KR); Sang O Pan, Gwangju (KR); Sung Yoon Park, Jeollanam-do (KR); Hyo Jeong Yun, Gwangju (KR); So Jeong Im, Gwangju (KR); Mi Ri Kim, Gwangju (KR); Yong Uk Kim, Jeollanam-do (KR); Dool-Ri Oh, Jeollanam-do (KR); Eun Jin Choi, Jeollanam-do (KR); Yu Jin Kim, Jeollanam-do (KR); Dong Hyuck Bae, Jeollanam-do (KR); KyoNyeo Oh, Gwangju (KR); Myung-A Jung, Jeollanam-do (KR); Ji Ae Hong, Jeollanam-do (KR); Hyun Mi Lee, Gwangju (KR); Rack Seon Seong, Jeollanam-do (KR)

(73) Assignee: JEONNAM BIOINDUSTRY FOUNDATION, Jeollanam-do (KR)

( * ) Notice: Subject to any disclaimer, the term of this patent is extended or adjusted under 35 U.S.C. 154(b) by 0 days.

(21) Appl. No.: 16/465,743

(22) PCT Filed: Nov. 8, 2017

(86) PCT No.: PCT/KR2017/012586
§ 371 (c)(1),
(2) Date: May 31, 2019

(87) PCT Pub. No.: WO2018/101630
PCT Pub. Date: Jun. 7, 2018

(65) Prior Publication Data
US 2019/0381123 A1 Dec. 19, 2019

(30) Foreign Application Priority Data

Dec. 1, 2016 (KR) ........................ 10-2016-0162678

(51) Int. Cl.
A61K 36/45 (2006.01)
A23L 33/105 (2016.01)
A61P 25/24 (2006.01)
A61K 9/00 (2006.01)

(52) U.S. Cl.
CPC ............ *A61K 36/45* (2013.01); *A23L 33/105* (2016.08); *A61K 9/0056* (2013.01); *A61P 25/24* (2018.01); *A23V 2002/00* (2013.01)

(58) Field of Classification Search
None
See application file for complete search history.

(56) References Cited

U.S. PATENT DOCUMENTS

2020/0121749 A1* 4/2020 Choi .................... A61K 9/0019

FOREIGN PATENT DOCUMENTS

| CN | 104814995 A | | 8/2015 |
|---|---|---|---|
| CN | 105169259 A | | 12/2015 |
| CN | 105497433 A | * | 4/2016 |
| CN | 105748666 A | | 7/2016 |
| CN | 106389785 A | * | 2/2017 |
| KR | 10-2007-0105626 A | | 10/2007 |
| KR | 10-2015-0113434 A | | 10/2015 |
| KR | 10-2016-0025414 A | | 3/2016 |
| KR | 10-2016-0119347 A | | 10/2016 |
| KR | 10-1799214 B1 | | 11/2017 |
| WO | WO 2016/032249 A1 | * | 3/2016 |

OTHER PUBLICATIONS

Oh, D. et al. Vaccinium bracteatum Leaf Extract Reverses Chronic Restraint Stress Induced Depression Like Behavior . . . Frontiers in Pharmacology 9:604, Jul. 9, 2018. (Year: 2018).*
Oh, D. et al. Antidepressant Effects of V. bracteatum via Protection Against Hydrogen Peroxide Induced Oxidative Stress and Apoptosis. The American J of Chinese Medicine 46(7)1499-1518, 2018. (Year: 2018).*
International Search Report from corresponding PCT Application No. PCT/KR2017/012586, dated Feb. 14, 2018, with English translation.
Jian Zhang et al: "Isolation and identification of antioxidant compounds in Vaccinium bracteatum Thunb. by UHPLC-Q-TOF LC/MS and their kidney damage protection". Journal of Functional Foods. vol. 11. Nov. 1, 2014.
Wonhwa Lee et al: "Antithrombotic and antiplatelet activities of orientin in vitro and in vivo", Journal of Functional Foods, vol. 17, Aug. 1, 2015 (Aug. 1, 2015), pp. 388-398, XP055552686.
Vi Liu et al: "Orientin improves depression-like behavior and BDNF in chronic stressed mice", Molecular Nutrition & Food Research, vol. 59, No. 6, Apr. 29, 2015 (Apr. 29, 2015), pp. 1130-1142, XP055552658.
Extended European Search Report from corresponding European Patent Application No. 17876695.2, dated Aug. 20, 2019.

* cited by examiner

*Primary Examiner* — Ralph J Gitomer
(74) *Attorney, Agent, or Firm* — Harness, Dickey & Pierce, P.L.C.

(57) ABSTRACT

The present invention provides a health functional food composition and a pharmaceutical composition for preventing and alleviating depression, both compositions using an extract of *Vaccinium bracteatum* Thunb. fruits, which are Korean natural resources, so as to be safely usable without toxicity and side effects.

1 Claim, 10 Drawing Sheets

CTL: Control
EO10: Escitalopram oxalate 10 mg/kg
VBFW100: Vaccinium bracteatum Thunb. fruit extract 100 mg/kg
VBFW200: Vaccinium bracteatum Thunb. fruit extract 200 mg/kg

**$P<0.01$ when compared with control
***$P<0.001$ when compared with control

CTL: Control
EO10: Escitalopram oxalate 10 mg/kg
VBFW100: Vaccinium bracteatum Thunb. fruit extract 100 mg/kg
VBFW200: Vaccinium bracteatum Thunb. fruit extract 200 mg/kg (B)

CTL: Control
EO10: Escitalopram oxalate 10 mg/kg
VBFW100: Vaccinium bracteatum Thunb. fruit extract 100 mg/kg
VBFW200: Vaccinium bracteatum Thunb. fruit extract 200 mg/kg

METHOD FOR ALLEVIATING DEPRESSION USING A HEALTH FUNCTIONAL FOOD CONTAINING *VACCINIUM BRACTEATUM* THUNB FRUIT EXTRACT

CROSS-REFERENCE TO RELATED APPLICATIONS

This application is a national phase application of PCT Application No. PCT/KR2017/012586, filed on Oct. 8, 2017, which claims priority to Korean Patent Application No. 10-2016-0162678, filed on Dec. 1, 2016. The entire disclosures of the applications identified in this paragraph are incorporated herein by reference.

FIELD

The present invention relates to a health functional food composition and a pharmaceutical composition containing a *Vaccinium bracteatum* Thunb. extract as an active ingredient for prevention and relief of depression and, more specifically, to a pharmaceutical composition and a health functional food composition for prevention and relief of depression, each of the compositions being capable of being safely used without toxicity and side effects by using a *Vaccinium bracteatum* Thunb. fruit extract from a natural substance.

BACKGROUND

Depression is a disease that causes various cognitive and psychosomatic symptoms including decline in enthusiasm and a feeling of sadness as main symptoms, resulting in deterioration of daily functioning. Depressive disorders are severe diseases that cause changes in feelings, thoughts, physical conditions, and behavior, thereby affecting the overall life of an individual. Depression is different from a temporary feeling of sadness. Depression is neither an expression of personal weakness nor can be eliminated by willingness.

Depressive disorders are one of the most common mental illnesses, and there are great differences in prevalence among countries. The lifetime prevalence of major depressive disorders is higher, 10.1-16.6%, in the United States, Europe, and New Zealand, but shows a low prevalence of 5% or less in non-western countries including Korea and China.

According to the epidemiologic survey of the mental health status by the Ministry of Health and Welfare in 2011, the lifetime prevalence of major depressive disorders was 6.7% and the annual prevalence was 3.1%, which were somewhat higher than those in the epidemiological study in 2006, and were similar or somewhat higher than those in non Western countries. The apparent causes of depression are not yet clear, but depression, like other mental illnesses, may be caused by a variety of biochemical, genetic, and environmental factors. Unlike other diseases, when depression is properly treated by a specialist, a considerable relief from depression can be expected and a return to normal life is possible.

*Vaccinium bracteatum* Thunb. is an angiosperm belonging to the class Dicotyledon and the order Ericales, and grows in mountains at the beach. The plant is 1-3 m in height, with small branches having grayish-brown to gray color and having little hair. Leaves are alternate, thick, elliptical or long elliptical, with a thick leather-like texture. The leaves have small saw-toothed edges and small glands on the lower part of the backside. The plant blooms in June, and flowers are reddish white. The plant has a drooped raceme with about ten bell-shaped flowers, and bracts remain. Fruits are berries, which are round, covered with white powder, and about 6 mm in diameter, and edible fruits ripen in October.

As the living standards of modern people have improved recently, there is a growing interest in natural resources that have little side effects and can be collected in nature. In particular, as research on health foods containing natural functional substances that predominantly contain nutrients necessary for the human body or specifically help the prevention and recovery of diseases has been actively conducted, *Vaccinium bracteatum* Thunb. is also researched for functions thereof. However, there is still lack of information on nutritional values or physiological functionality thereof.

SUMMARY

Technical Problem

An aspect of the present invention is to provide a functional food composition and a pharmaceutical composition using *Vaccinium bracteatum* Thunb., which is a natural resource that is not accurately known for physiologically active functions thereof and, specifically, to provide a functional food composition and a pharmaceutical composition for prevention and relief of depression, each of the compositions containing, as an active ingredient, a *Vaccinium bracteatum* Thunb. fruit extract, which is obtained by extracting effective ingredients from *Vaccinium bracteatum* Thunb. fruits and thus can be safely used without toxicity and side effects.

Technical Solution

The present invention provides a health functional food composition and a pharmaceutical composition for prevention and relief of depression, each of which can be safely used without toxicity and side effects by using a *Vaccinium bracteatum* Thunb. fruit extract from a Korean natural resource. In accordance to an aspect, the present invention provides a health functional food composition and a pharmaceutical composition for prevention and relief of depression, each of which contains a *Vaccinium bracteatum* Thunb. fruit extract as an active ingredient.

As for the extraction method for the pharmaceutical composition and the functional food composition having functions of preventing and relieving depression, distilled water was added to *Vaccinium bracteatum* Thunb. fruits, followed by heating and extraction using a reflux extractor for 3 hours after the temperature rose to 100° C. or higher.

The present invention provides a health functional food composition and a pharmaceutical composition for prevention and relief of depression, each of the compositions containing 0.01-99.9 wt % of an extract containing, as an active ingredient, an extract soluble in any one of water, methanol, ethanol, propanol, isopropanol, butanol, or a mixture solvent thereof.

The compositions may be manufactured into a form of at least one selected from a tablet, a capsule, a soft capsule, granules, a liquid preparation, or a drink.

Advantageous Effects

The *Vaccinium bracteatum* Thunb. fruit extract of the present invention decreased the immobility time during which the limbs do not move, showing an excellent anti-depressive effect compared with escitalopram oxalate as a comparison group. In animal experiments, when the *Vaccinium bracteatum* Thunb. fruit extract and escitalopram oxalate were administered, the *Vaccinium bracteatum* Thunb. fruit extract administration groups showed an increase tendency of norepinephrine (noradrenaline) concentration compared with the control group, confirming that the *Vaccinium bracteatum* Thunb. fruit extract has an effect as an anti-depressive preparation by increasing the concentration of norepinephrine (noradrenaline).

DETAILED DESCRIPTION

1. Preparation of *Vaccinium bracteatum* Thunb. Fruit Extract

Figure 1:
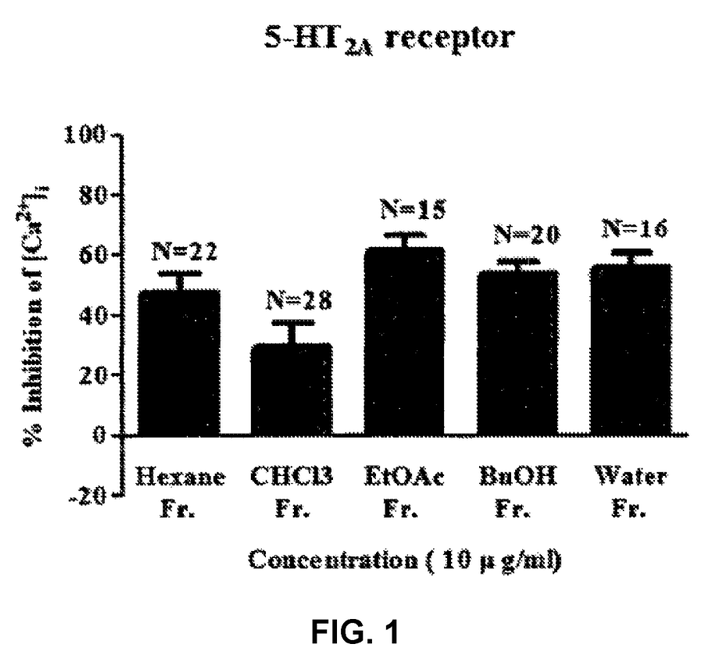
FIG. 1 shows a schematic diagram illustrating a *Vaccinium bracteatum* Thunb. fruit extract.

FIG. 1 shows a procedure of obtaining a *Vaccinium bracteatum* Thunb. fruit extract. 30 L of distilled water was added to 2.0 kg of *Vaccinium bracteatum* Thunb. fruits, followed by heating and extraction using a reflux extractor for 3 hours after the temperature rose to 100° C. or higher. The obtained extract was subjected to filtration under reduced pressure and then concentration under reduced pressure, thereby obtaining 107.02 g of a concentrate.

Figure 2:
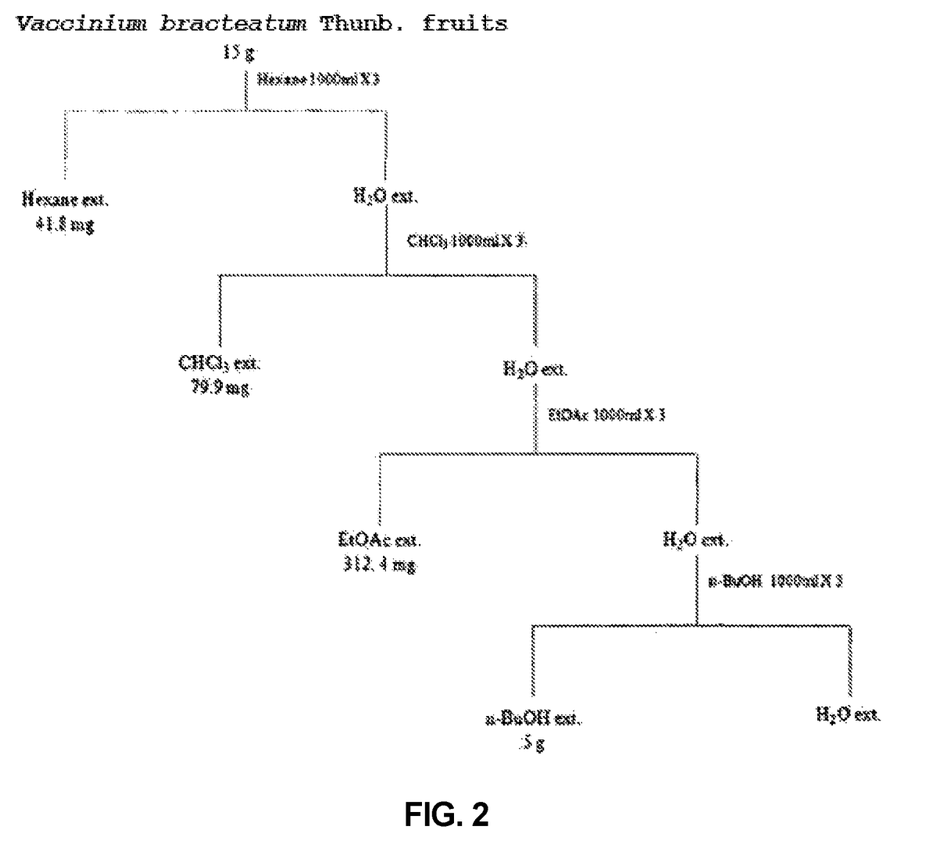
FIG. 2 shows a schematic diagram illustrating the fractions of a *Vaccinium bracteatum* Thunb. Fruit extract.

2. Preparation of Polar Solvent- and Nonpolar Solvent-Soluble Fractions of *Vaccinium bracteatum* Thunb. Fruits As shown in FIG. 2, the preparation of fractions of the *Vaccinium bracteatum* Thunb. fruit extract by performing systemic fraction from the *Vaccinium bracteatum* Thunb. fruit extract will be specifically described below. The concentrate was sufficiently suspended in water and subjected to primary solvent carryover three times using a 2-fold volume of hexane, leading to separation into a water layer and a hexane ext. (41.8 mg). The water layer was again subjected to secondary solvent carryover three times using a 2-fold volume of chloroform, thereby securing a $CHCl_3$ ext. (79.9 mg). Tertiary solvent carryover using ethyl acetate was performed three times, thereby securing an EtOAc ext. (312.4 mg). Last, quaternary solvent carryover using n-butanol was performed three times, thereby securing an n-BuOH ext. (5 g).

3. Animals and Breeding

As test animals for determining an anti-depressive effect of the *Vaccinium bracteatum* Thunb. fruit extract, 6-week-old ICR male mice were purchased from SAMTACO (Korea), and acclimated for 1 week in an animal breeding room in predetermined conditions (temperature: 22±2° C., humidity: 50±5%, 12 hr-light/dark cycle) before use.

4. Animal Behavior Test on Anti-Depression Using *Vaccinium bracteatum* Thunb. Fruit Extracts The ICR male mice were orally administered with the *Vaccinium bracteatum* Thunb. fruit extract of the present invention. For a comparative group, escitalopram oxalate used an anti-depressant was orally administered. These were administered for 6 days according to the test.

Before drug administration, for the pre-test (pre-swim), tap water around 25° C. was poured into a cylindrical water tank (20 cm in diameter, 40 cm in height) from the bottom of the cylinder to 15 cm, and then the mice were put into the water tank, forced to swim for 15 minutes, taken out from the water, wiped with a dry towel, and then returned to breeding boxes. After 6 days of drug administration, the present test (post-swim) was carried out. The mice were put into the cylinder, and forced to swim for 6 minutes under videotaping. The recorded image was analyzed excluding the first minute therefrom, and animal behavior during the last 5 minutes was classified into 3 types: immobility behavior (the mouse only floated near the surface of the water, slightly moving while only a part of the upper body including the face was above water), swimming behavior (the mouse moved horizontally around the cylinder moving the front and hind legs in a swimming motion), and climbing behavior (the mouse scratched the wall, somewhat violently kicking the front extremities to move remain above water). The duration of each behavior type was measured.

Figure 3:
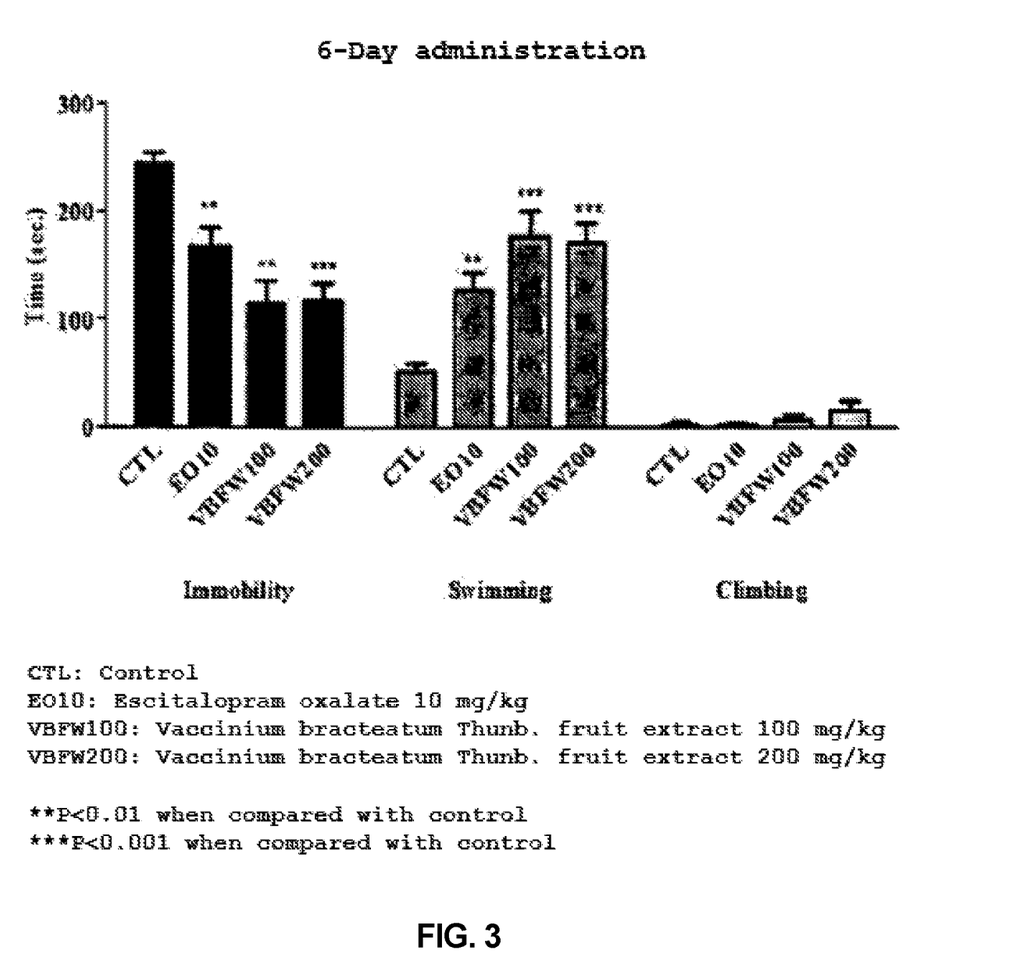
FIG. 3 shows a graph illustrating the comparison of immobility time, swimming time, and climbing time in the forced swimming test among white mice administered with *Vaccinium bracteatum* Thunb. fruit extracts of the present invention for 6 days, control group mice, and escitalopram oxalate administration group mice.

FIG. 3 shows a graph illustrating the comparison of immobility time, swimming time, and climbing time in the forced swimming test among white mice administered with *Vaccinium bracteatum* Thunb. fruit extracts of the present invention for 6 days, control group mice, and escitalopram oxalate administration group mice. As shown in FIG. 3, during the forced swimming after the administration of each drug for 6 days, the immobility time was 169.65±7.15 seconds for escitalopram oxalate as the comparison group, and 114.98±9.26 seconds and 118.29±6.35 seconds for *Vaccinium bracteatum* Thunb. fruit extracts (100 and 200 mg/kg p.o), showing significant reductions, compared with the control group (245.48±4.05 seconds) ($P<0.01$ and P<0.001). The swimming time was 128.16±6.65 seconds for escitalopram oxalate as the comparison group, and 177.07±9.79 seconds and 172.23±6.72 seconds for *Vaccinium bracteatum* Thunb. fruit extracts (100 and 200 mg/kg p.o), showing significant increases, compared with the control group (51.82±3.38 seconds) (P<0.01 and P<0.001).

As seen above, it was confirmed that the *Vaccinium bracteatum* Thunb. fruit extract of the present invention decreased the immobility time during which the limbs do not move, showing an excellent anti-depressive effect compared with escitalopram oxalate as the comparison group.

5. Measurement of Norepinephrine (NE) and Corticosterone (COR) in Plasma Using *Vaccinium bracteatum* Thunb. Fruit Extract The effects on concentration changes of the neurotransmitter NE associated with depression and the stress hormone COR in normal conditions were measured by isolating plasma from the mice after 6 day-administration of each drug and using the Abnova ELISA kit according to the instruction of the manufacturer.

Figure 4:
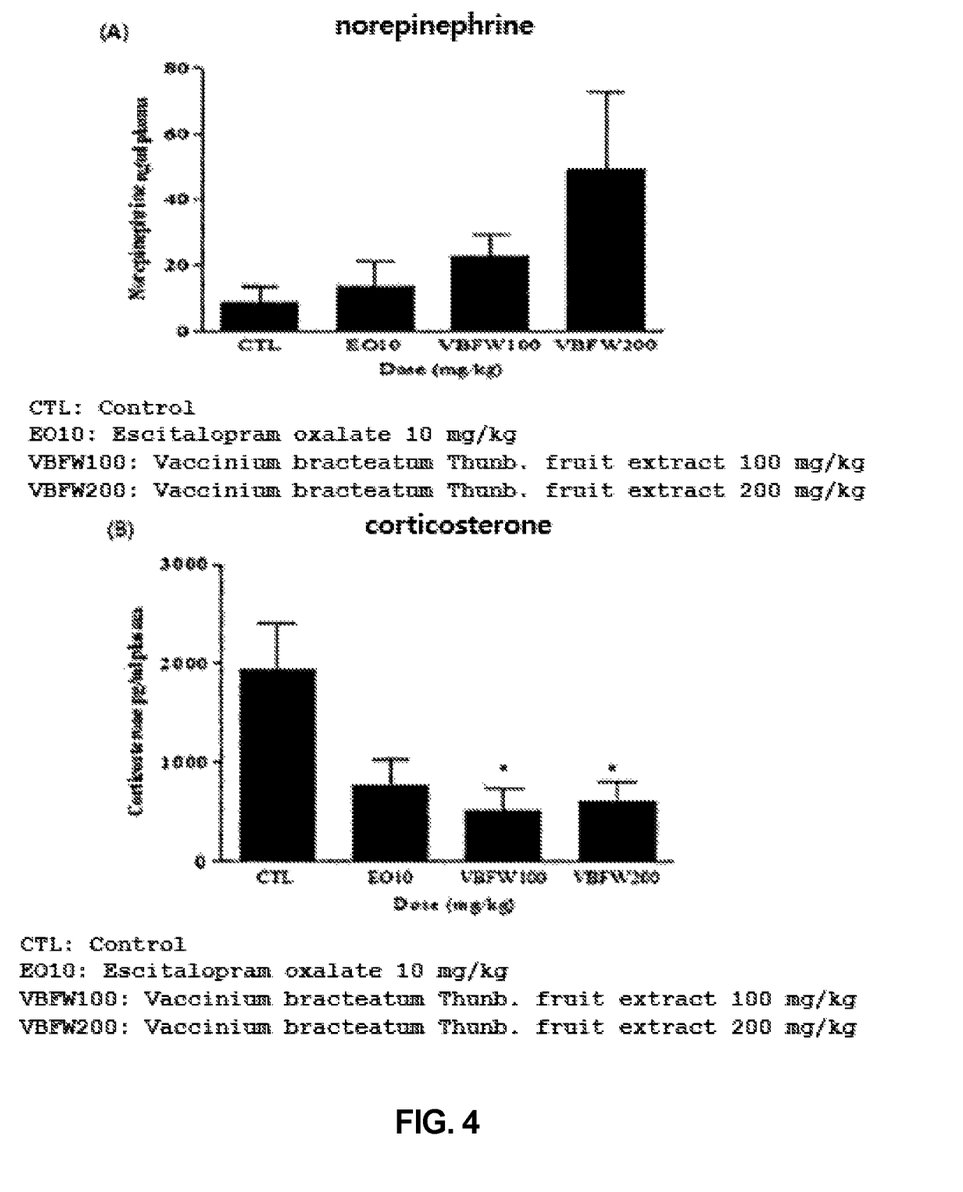
FIG. 4 shows graphs illustrating the comparison of the increase or decrease in the neurotransmitter and the stress hormone in the blood among mice administered with the *Vaccinium bracteatum* Thunb. fruit extracts of the present invention, control group mice, and escitalopram oxalate administration group mice.

FIG. 4 shows graphs illustrating the comparison of the increase or decrease in the neurotransmitter and the stress hormone in the blood among mice administered with the *Vaccinium bracteatum* Thunb. fruit extracts of the present invention, control group mice, and escitalopram oxalate administration group mice. The anti-depressive effects of the *Vaccinium bracteatum* Thunb. fruit extract on the variations of NE and COR in normal conditions were investigated. The reason for a feeling of sadness is due to a small amount of serotonin or norepinephrine (noradrenaline) secreted externally from brain neurons to the outside. As a result of investigating an increase or decrease in the neurotransmitter norepinephrine through the *Vaccinium bracteatum* Thunb. fruit extract, as shown in FIG. 4(A), when normal animals were administered with the *Vaccinium bracteatum* Thunb. fruit extracts (100 and 200 mg/kg) and escitalopram oxalate (10 mg/kg), the *Vaccinium bracteatum* Thunb. fruit extracts (100 and 200 mg/kg) administration groups showed an increase tendency of NE concentration compared with the control group. These results indicate that the *Vaccinium bracteatum* Thunb. fruit extract is effective as an antidepressant by increasing the concentration of NE.

In addition, as shown in FIG. 4(B), the level of the stress hormone corticosterone was significantly reduced in the *Vaccinium bracteatum* Thunb. fruit extract (100 and 200 mg/kg) administration groups compared with the control group, and the comparative group of escitalopram oxalate showed a decrease tendency of corticosterone compared with the control group, with no significance. Therefore, considering that the corticosterone levels are known to increase when an individual feels stressed, these results suggest that the *Vaccinium bracteatum* Thunb. fruit extract would also show an anti-depressive effect in stress depression models.

6. Investigation of Stress Relieving Activity in Brain Neurons Using *Vaccinium bracteatum* Thunb. Fruit Extract SH-SY5Y cells (neuroblastoma, human dopaminergic neuronal cells) were incubated in MEM medium containing 1% antimycotics/antibiotics and 10% FBS. The cells were seeded at a density of $10^5$ cell/ml in a 96-well plate, and then incubated for 24 hours.

To investigate the cytotoxicity of the *Vaccinium bracteatum* Thunb. fruit extract on neurons, the cells were treated with the extract according to the concentration. Cell viability was evaluated using an MTT assay 24 hours after the treatment with the *Vaccinium bracteatum* Thunb. fruit extract.

Figure 5:
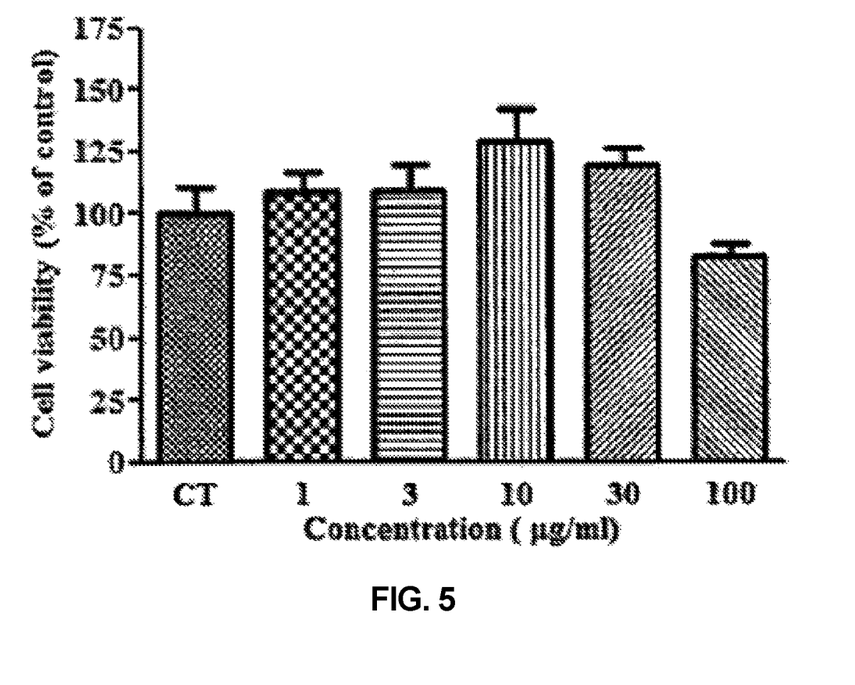
FIG. 5 shows a graph illustrating the cytotoxicity degree of the *Vaccinium bracteatum* Thunb. fruit extract of the present invention on SH-SY5Y cells (neuroblastoma, human dopaminergic neuronal cells).

FIG. 5 shows a graph illustrating the cytotoxicity degree of the *Vaccinium bracteatum* Thunb. fruit extract of the present invention on SH-SY5Y cells (neuroblastoma, human dopaminergic neuronal cells).

The cytotoxicity of the *Vaccinium bracteatum* Thunb. fruit extract was measured using MTT to determine the degree of cytotoxicity thereof, thereby setting the maximum safety range of use concentration thereof. The cell line used was SH-SY5Y cells, and the cells were treated with the *Vaccinium bracteatum* Thunb. fruit hot-water extract at concentrations of 1, 3, 10, 30, and 100 μg/ml to investigate cytotoxicity. The *Vaccinium bracteatum* Thunb. fruit extract at 1, 3, 10, and 30 μg/ml showed no significant difference compared to the control (0 μg/ml). However, the *Vaccinium bracteatum* Thunb. fruit extract at 100 μg/ml showed a reduced cell viability, although no significant difference was shown compared to the control. From the above results, tests were performed within 30 μg/ml.

To determine the effect of *Vaccinium bracteatum* Thunb. fruit extract on neuronal apoptosis caused by oxidative stress, the use concentration of hydrogen peroxide was first determined. For the determination, the cells were treated with hydrogen peroxide at different concentrations for 24 hours to investigate cell cytotoxicity, and the concentration of *Vaccinium bracteatum* Thunb. fruit extract showing 50-60% cytotoxicity was determined and used in the test. For the test to investigate the neuronal protective effect of the *Vaccinium bracteatum* Thunb. fruit extract, the test cell line (SH-SY5Y cell line) was dispensed in a 96-well microplate, incubated for 24 hours, treated with the *Vaccinium bracteatum* Thunb. fruit extract for 2 hours, treated with 10 μM $H_2O_2$, and incubated for 24 hours. After 24 hours, cell viability was determined using an MTT assay.

Figure 6A:
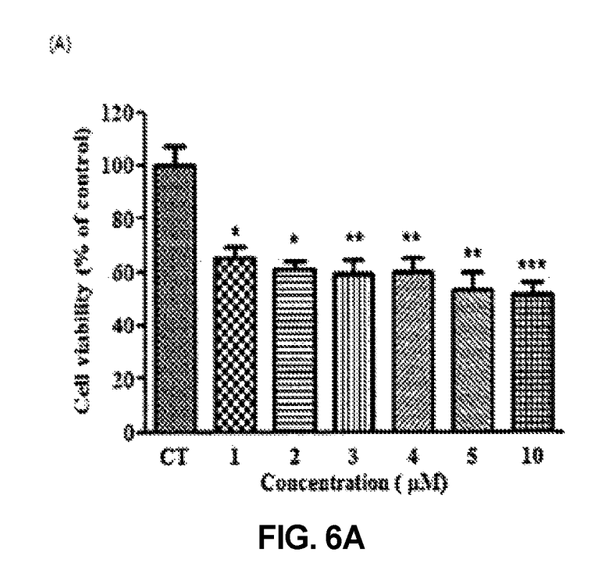
FIGS. 6A and 6B show graphs illustrating the neuronal protective effect of the *Vaccinium bracteatum* Thunb. fruit extract against oxidative stress induced through the treatment with hydrogen peroxide.
Figure 6B:
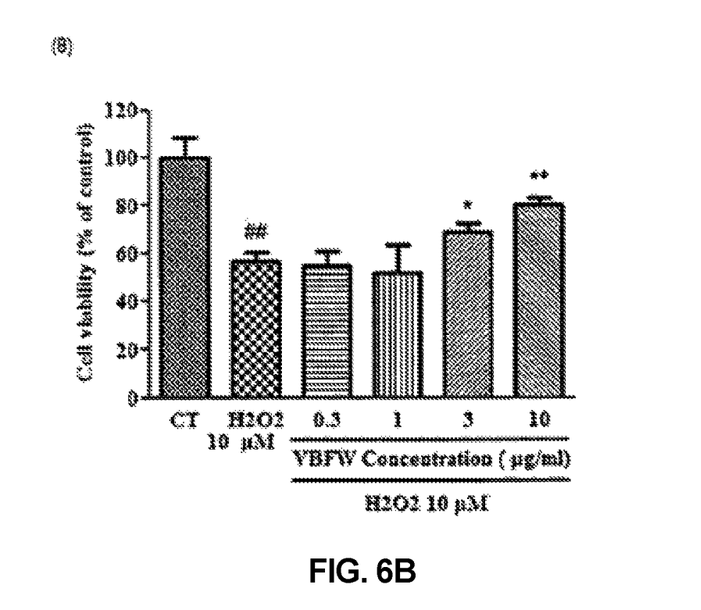

FIG. 6 shows graphs illustrating the neuronal protective effect of the *Vaccinium bracteatum* Thunb. fruit extract against oxidative stress induced through the treatment with hydrogen peroxide. In FIG. 6A, for the determination of the use concentration of hydrogen peroxidase, the cell line (SH-SY5Y cells) used was treated with $H_2O_2$ according to the concentration to investigate cytotoxicity, and as a result, $H_2O_2$ at 10 μM showed a cell viability of 50-60%, indicating significant cytotoxicity, compared with the control (0 μg/ml), and thus were used for the test. FIG. 6B confirmed that in the treatment with the *Vaccinium bracteatum* Thunb. fruit extract together with 10 μM hydrogen peroxide ($H_2O_2$), the *Vaccinium bracteatum* Thunb. fruit hot-water extract at 0.3, 1, 3, and 10 μg/ml showed cell viability of 54.75±2.85%, 52.18±5.05%, 69.01±1.48%, and 80.24±1.14%, respectively, indicating significant increases (P<0.05 or P<0.01).

To investigate the resistance activity of the *Vaccinium bracteatum* Thunb. fruit extract against mental stress at the cellular level, the test was conducted to investigate the protective effect on neuronal damages caused by the stress hormone corticosterone. The cells were treated with corticosterone at different concentrations for 24 hours to investigate cell cytotoxicity, and the concentration of corticosterone showing 50-60% cytotoxicity was determined, and used in the test. For the test to investigate the protective effect of the *Vaccinium bracteatum* Thunb. fruit extract, the test cell line (SH-SY5Y cell line) was dispensed in a 96-well microplate, incubated for 24 hours, treated with the *Vaccinium bracteatum* Thunb. fruit extract for 2 hours, treated with 1 μM corticosterone, and incubated for 24 hours. After 24 hours, cell viability was determined using an MTT assay.

Figure 7A:
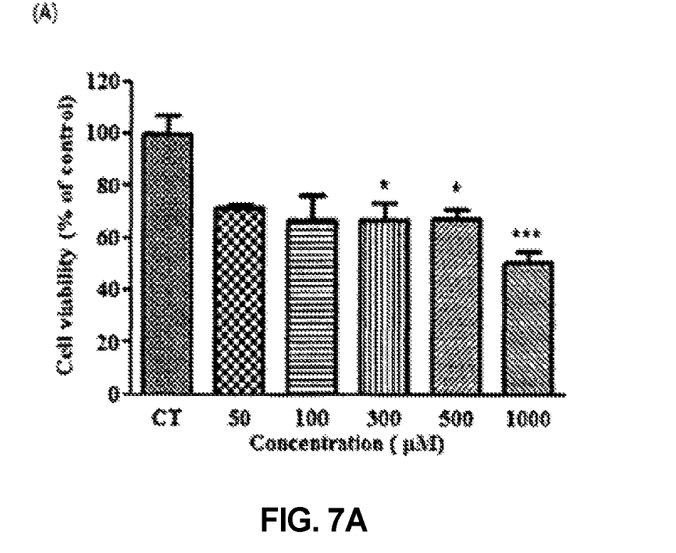
FIGS. 7A and 7B show graphs illustrating the intracellular stress induction through the treatment with the mental stress hormone corticosterone and the neuronal protective effect of the *Vaccinium bracteatum* Thunb. fruit extract according to the concentration.
Figure 7B:
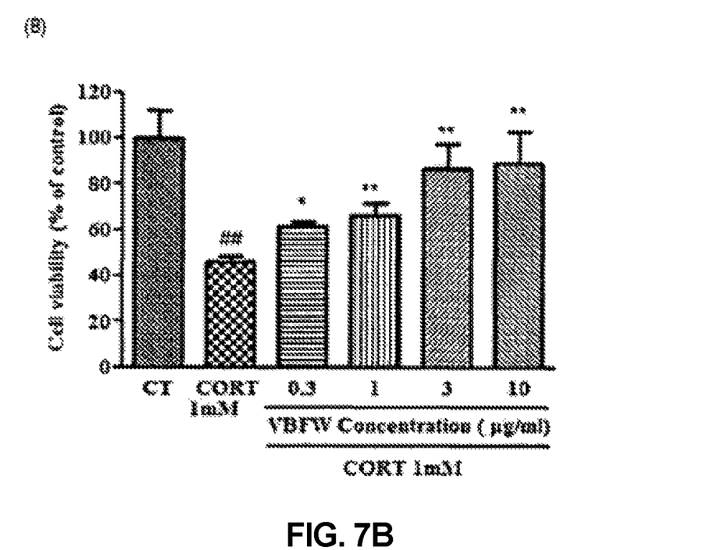

FIG. 7 shows graphs illustrating the intracellular stress induction through the treatment with the mental stress hormone corticosterone and the neuronal protective effect of the *Vaccinium bracteatum* Thunb. fruit extract according to the concentration. For the determination of the use concentration of the stress hormone corticosterone, SH-SY5Y cells were treated with corticosterone at 50, 100, 300, 500, and 1000 µM to investigate cytotoxicity, and cell viability was reduced in corticosterone at 300, 500, and 1000 µM compared with the control (0 µg/ml), and 1 mM corticosterone showing 50-60% cytotoxicity was used for the test. FIG. 7B confirmed that in the treatment with the *Vaccinium bracteatum* Thunb. fruit extract together with corticosterone, the *Vaccinium bracteatum* Thunb. fruit hot-water extract at 0.3, 1, 3, and 10 µg/ml showed cell viability of 63.28±0.42%, 66.55±2.21%, 86.91±4.27%, and 89.08±5.47%, respectively, indicating significant increases (P<0.05 or P<0.01).

7. Measurement of Intracellular $Ca^{2+}$ Activity Using *Vaccinium bracteatum* Thunb. Fruit Extract in $5\text{-}HT_{1A}$ or $5\text{-}HT_{2A}$ Receptor Gene-Expressed Cell Line CHO-K1 cell line (Chinese Hamster Ovary Cells) was purchased from ATCC, and dispensed using a culture liquid (RPMI 1640, fetal bovine serum 10%, penicillin 100 IU/ml, streptomycin 100 µg/ml) in a 96-well black wall/clear bottom (BD Falcon), and then incubated in 37° C., 5% $CO_2$ incubator for 24 hours. The cells, in which serotonin 1A receptor ($5\text{-}HT_{1A}$ receptor) or serotonin 2A receptor ($5\text{-}HT_{2A}$ receptor) cDNA was transiently expressed in cells using the plasmid transfection reagent lipofectamine 2000 for 48 hours, were used for the test.

Before fluorescent staining, the cells were washed once with HEPES-buffered solution (155 mM NaCl, 2 mM $CaCl_2$), 1 mM $MgCl_2$, 3 mM KCl, 10 mM HEPES, 10 mM Glucose, pH 7.4), treated with Fura-2/AM at a final concentration of 5 µM, which is a fluorescent dye for measuring intracellular calcium concentration, and then incubated in the 37° C., 5% $CO_2$ incubator for 60 minutes while the light was blocked. After 60 minutes, the cells were washed once with HEPES-buffered solution, and then the intracellular calcium concentration was determined by the selective exposure to the light at 340/380 nm using a high-throughput system (HTS) system and then the measurement of the 340/380 nm ratio analyzed using a digital fluorescence analyzer. The Fura-2/AM present in cells is excited at 340 nm in the state combined with $Ca^{2+}$, and excited at 380 nm in the unbound state, and therefore, an increase in the 340/380 nm ratio value means that fura-2/AM combined with intracellular $Ca^{2+}$ is increased.

Figure 8:
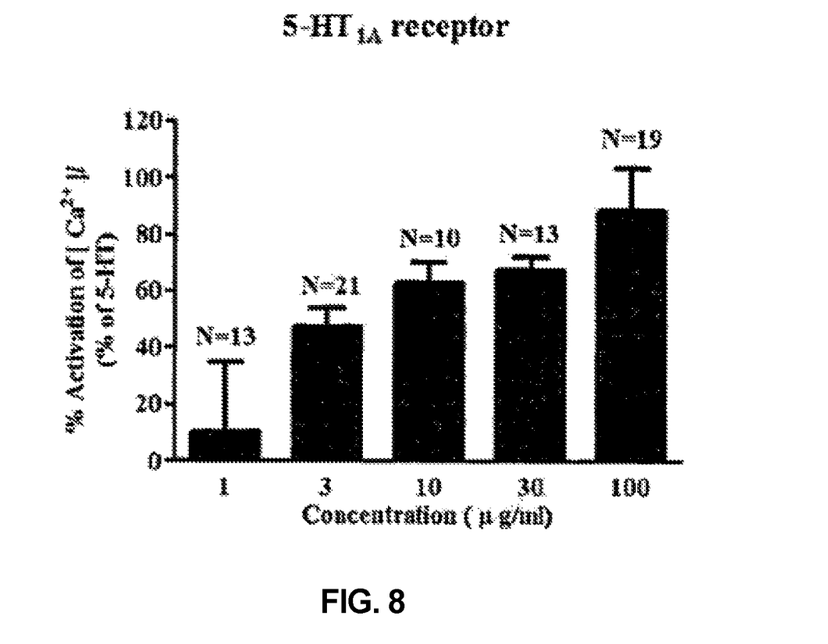
FIG. 8 shows a graph illustrating the effect of the *Vaccinium bracteatum* Thunb. fruit extract of the present invention to increase the 5-HT-induced intracellular $Ca^{2+}$ increase in a dose-dose-dependent manner in the 5-$HT_{1A}$ receptor gene-expressed cell line.
Figure 9:
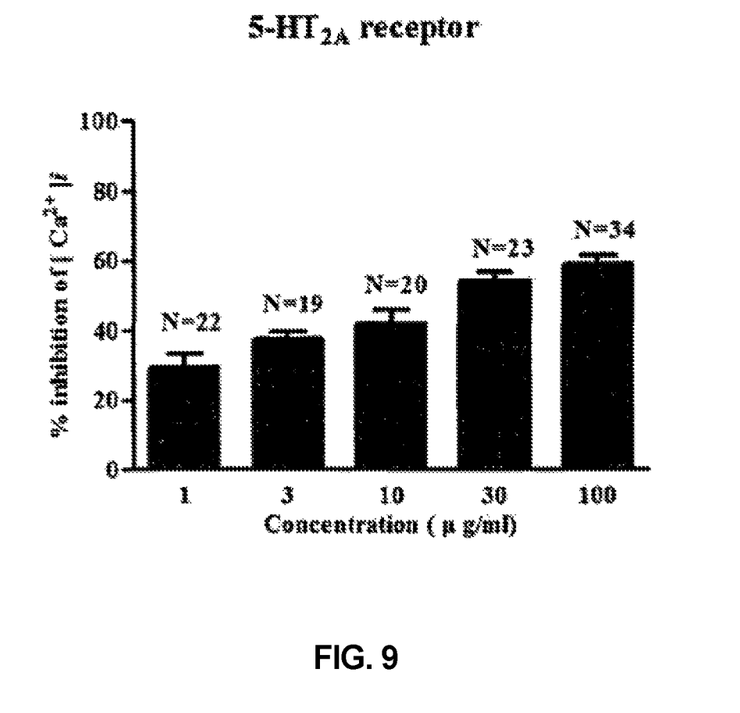
FIG. 9 shows a graph illustrating the effect of the *Vaccinium bracteatum* Thunb. fruit extract of the present invention to inhibit the 5-HT-induced intracellular $Ca^{2+}$ increase in a dose-dependent manner in the 5-$HT_{2A}$ receptor gene-expressed cell line.

The value obtained by the treatment with 100 µM serotonin (5-HT) was used for a control, and the change in amount of intercellular calcium was investigated after the cells were pre-treated with the *Vaccinium bracteatum* Thunb. fruit extract at 1, 3, 10, 30, and 100 µg/ml for 1 minute and then 100 µM 5-HT. In FIGS. 8 and 9, the number on the error bar of each item means the number of cells used in the test.

FIG. 8 shows a graph illustrating the effect of the *Vaccinium bracteatum* Thunb. fruit extract of the present invention to increase the 5-HT-induced intracellular $Ca^{2+}$ increase in a dose-dose-dependent manner in the $5\text{-}HT_{1A}$ receptor gene-expressed cell line. In serotonin-induced intracellular $Ca^{2+}$ in the $5\text{-}HT_{1A}$ receptor, the *Vaccinium bracteatum* Thunb. fruit extract activated the intracellular $Ca^{2+}$ compared with serotonin, and thus the effect of the *Vaccinium bracteatum* Thunb. fruit extract as a partial agonist of the $5\text{-}HT_{1A}$ receptor was confirmed. As shown in FIG. 8, the intracellular $Ca^{2+}$ induced by $5\text{-}HT_{1A}$ receptor-specific serotonin was activated by 10.31±6.86%, 47.45±1.45%, 62.73±2.37%, 67.08±1.36%, and 88.09±3.50%, using the *Vaccinium bracteatum* Thunb. fruit extract at 1, 3, 10, 30, and 100 µg/ml, in a dose-dependent manner, compared with the control treated with 100 µM serotonin.

8. Measurement of Intracellular $Ca^{2+}$ Activity in $5\text{-}HT_{2A}$ Receptor Gene-Expressed Cell Line Using Solvent Fractions of *Vaccinium bracteatum* Thunb. Extract CHO-K1 cell line (Chinese Hamster Ovary Cells) was purchased from ATCC, and dispensed using a culture liquid (RPMI 1640, fetal bovine serum 10%, penicillin 100 IU/ml, streptomycin 100 µg/ml) in a 96-well black wall/clear bottom (BD Falcon), and then incubated in 37° C., 5% $CO_2$ incubator for 24 hours. The cells, in which serotonin 2A receptor ($5\text{-}HT_{2A}$ receptor) cDNA was transiently expressed in cells using the plasmid transfection reagent lipofectamine 2000 for 48 hours, were used for the test.

Before fluorescent staining, the cells were washed once with HEPES-buffered solution (155 mM NaCl, 2 mM $CaCl_2$), 1 mM $MgCl_2$, 3 mM KCl, 10 mM HEPES, 10 mM Glucose, pH 7.4), treated with Fura-2/AM at a final concentration of 5 µM, which is a fluorescent dye for measuring intracellular calcium concentration, and then incubated in the 37° C., 5% $CO_2$ incubator for 60 minutes while the light was blocked. After 60 minutes, the cells were washed once with HEPES-buffered solution, and then the intracellular calcium concentration was determined by the selective exposure to the light at 340/380 nm using a high-throughput system (HTS) system and then the measurement of the 340/380 nm ratio analyzed using a digital fluorescence analyzer. The Fura-2/AM present in cells is excited at 340 nm in the state combined with $Ca^{2+}$, and excited at 380 nm in the unbound state, and therefore, an increase in the 340/380 nm ratio value means that fura-2/AM combined with intracellular $Ca^{2+}$ is increased.

The treatment with 100 µM serotonin (5-HT) was used as a control, and the change in amount of intercellular calcium was investigated after the cells were pre-treated with the hexane, chloroform, ethyl acetate, butanol, and water fractions of the *Vaccinium bracteatum* Thunb. fruit extract and then 100 µM 5-HT.

FIG. 9 shows a graph illustrating the effect of the *Vaccinium bracteatum* Thunb. fruit extract of the present invention to inhibit the 5-HT-induced intracellular $Ca^{2+}$ increase in a dose-dependent manner in the $5\text{-}HT_{2A}$ receptor gene-expressed cell line. It was confirmed in FIG. 9 that, in serotonin-induced intracellular $Ca^{2+}$ in the $5\text{-}HT_{2A}$ receptor, the *Vaccinium bracteatum* Thunb. fruit extract inhibited the intracellular $Ca^{2+}$, compared with serotonin, in a dose-dependent manner. As shown in FIG. 9, the intracellular $Ca^{2+}$ concentration induced by $5\text{-}HT_{2A}$ receptor-specific serotonin was inhibited by 29.15±0.81%, 37.53±0.49%, 42.09±0.92%, 54.39±0.55%, and 59.03±0.48%, using the *Vaccinium bracteatum* Thunb. fruit extract at 1, 3, 10, 30, and 100 µg/ml, in a dose-dependent manner, compared with the control treated with 100 µM serotonin.

Figure 10:
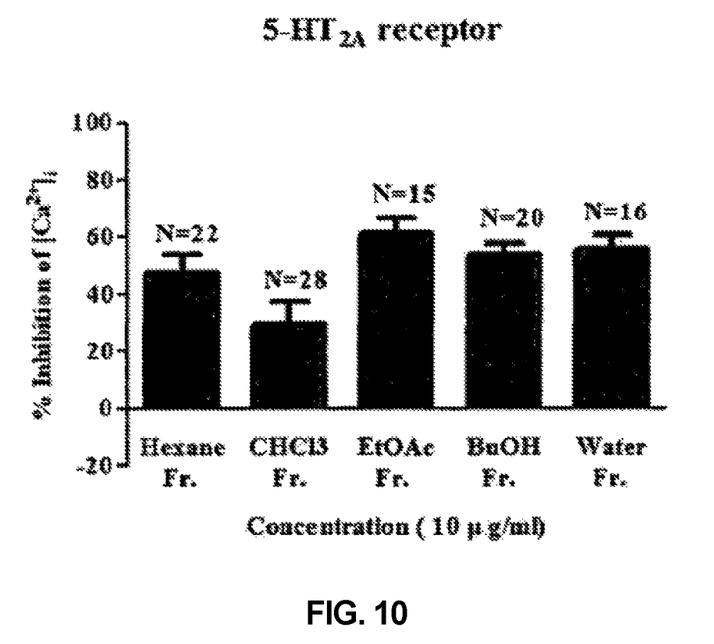
FIG. 10 shows a graph illustrating the effect of the fractions of the *Vaccinium bracteatum* Thunb. fruit extract of the present invention to inhibit the 5-HT-induced intracellular $Ca^{2+}$ increase in the 5-$HT_{2A}$ receptor gene-expressed cell line.

FIG. 10 shows a graph illustrating the effect of the fractions of the *Vaccinium bracteatum* Thunb. fruit extract of the present invention to inhibit the 5-HT-induced intracellular $Ca^{2+}$ increase in the $5\text{-}HT_{2A}$ receptor gene-expressed cell line. In FIG. 10, the number on the error bar of each item means the number of cells used in the test. FIG. 10 shows the results on the intracellular $Ca^{2+}$ concentration inhibitory activity of the solvent fractions of the *Vaccinium bracteatum* Thunb. fruit extract, compared with serotonin, in the serotonin-induced $Ca^{2+}$ increase in the $5\text{-}HT_{2A}$ receptor. As shown in FIG. 10, among the solvent fractions, such as hexane, chloroform, ethyl acetate, butanol, and water fractions, of the *Vaccinium bracteatum* Thunb. fruit extract, the ethyl acetate and butanol fractions showed the highest inhibitory activity on the serotonin-induced intracellular $Ca^{2+}$ increase in the $5\text{-HT}_{2A}$ receptor.

9. Manufacturing of Medicines or Health Foods Using *Vaccinium bracteatum* Thunb. Fruit Extract A pharmaceutical composition or health food composition containing a *Vaccinium bracteatum* Thunb. fruit extract as an active ingredient for immunity enhancement may be manufactured in the form of a tablet, a capsule, a soft capsule, granules, or a liquid preparation. According to another proper embodiment, the composition may be manufactured as a drink additive. The medicine or health food for immunity enhancement may be manufactured by formulation into a powder, granules, a tablet, a capsule, a suspension, an emulsion, a syrup, an aerosol, a percutaneous medicine, a suppository, or a sterile injection solution such that the composition containing the *Vaccinium bracteatum* Thunb. fruit extract as an active ingredient is contained at 0.01-99.9 wt %.

The sterile injection solution can be manufactured by containing 0.01-99.9 wt % of the pharmaceutical composition and mixing the pharmaceutical composition with 99.9-0.01 wt % of purified water or glucose. The capsule may be manufactured by containing 0.01-99.9 wt % of the pharmaceutical composition after freeze drying and mixing the pharmaceutical composition with 99.9-0.01 wt % of a vitamin or calcium agent.

The daily dose of the prepared pharmaceutical composition corresponds to a content in which the extract is contained at 10-2000 mg/kg body weight. Furthermore, a health functional food containing 0.01-99.9 wt % of the pharmaceutical composition for prevention or relief of depression symptoms can also be manufactured.

INDUSTRIAL APPLICABILITY

The present invention provides a health functional food composition containing a *Vaccinium bracteatum* Thunb. fruit extract as an active ingredient for relief of depression causes and symptom diseases, and thus can replace the raw materials for a plant growing in nature, thereby expecting the reduction of manufacturing and production costs and the import substitution and export effects through industrialization, so that the present invention is industrially applicable.

What is claimed is:

1. A method for relief of depression comprising:
administering, to a subject in need thereof, a composition comprising an effective amount of *Vaccinium bracteatum* Thunb. fruit extract as an active ingredient, wherein the *V. bracteatum* Thunb. fruit extract is an ethyl acetate fraction or butanol fraction of a water extract.

* * * * *